United States Patent [19]

Ratton

[11] Patent Number: 4,508,922
[45] Date of Patent: Apr. 2, 1985

[54] PROCESS FOR THE PREPARATION OF OPTIONALLY HALOGENATED ANILINES

[75] Inventor: Serge Ratton, Lyons, France

[73] Assignee: Rhone-Poulenc Agrochimie, Lyons, France

[21] Appl. No.: 508,716

[22] Filed: Jun. 28, 1983

[30] Foreign Application Priority Data

Jun. 29, 1982 [FR] France .................. 82 11617

[51] Int. Cl.³ .................................. C07C 85/04
[52] U.S. Cl. ........................... 564/407; 564/404
[58] Field of Search .............. 564/404, 407, 408

[56] References Cited

U.S. PATENT DOCUMENTS

| | | | |
|---|---|---|---|
| 2,159,370 | 5/1939 | Dreisbach | 564/407 |
| 2,678,314 | 12/1950 | Taylor | 546/7 |
| 3,637,711 | 3/1968 | Budde et al. | 546/7 |
| 4,117,013 | 9/1978 | Anderson | 564/481 |

FOREIGN PATENT DOCUMENTS 1601746 11/1981 United Kingdom ............. 564/407

OTHER PUBLICATIONS

CA: 94, 64770z, Kondratov et al.

*Primary Examiner*—Charles F. Warren
*Assistant Examiner*—Harry B. Shubin

*Attorney, Agent, or Firm*—Burns, Doane, Swecker & Mathis

[57] ABSTRACT

Process for the manufacture of an optionally halogenated aniline of the formula:

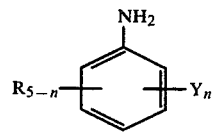

in which Y=halogen, R=H, alkyl ($C_1$-$C_4$) or alkoxy ($C_1$-$C_4$) and n=0 to 5.

Halogenobenzenes of the formula:

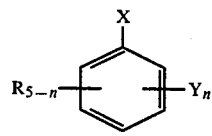

in which Y, R and n are as above and X=halogen, are subjected to ammonolysis with aqueous ammonia solution, in the presence of copper and 8-hydroxyquinoline.

The process can be used, in particular, for the preparation of 3,5-dichloroaniline.

14 Claims, No Drawings

PROCESS FOR THE PREPARATION OF OPTIONALLY HALOGENATED ANILINES

The present invention relates to a new process for the preparation of optionally halogenated anilines by the ammonolysis of a (poly)halogenobenzene. These anilines, and especially 3,5-dichloroaniline, are intermediates for the manufacture of agrochemical active ingredients.

It is known to prepare 3,5-dihalogenoanilines by reacting ammonia gas, liquid ammonia or aqueous ammonia solution with the corresponding halogenobenzenes, in the presence of a copper catalyst, it being possible for the copper to be associated with a complexing agent. This type of reaction has a low productivity under economic conditions, the reaction being slow, having an inadequate selectivity and having a yield which is limited, in particular, by subsequent ammonolysis of the good product obtained. This is particularly clear in the case of 3,5-dichloroaniline, a large proportion of 1,3-diamino-5-chlorobenzene being obtained in the preparation of this compound by this process. These disadvantages therefore prevent this method from being used on an industrial scale under good conditions. Now, the products resulting from this reaction, and especially 3,5-dichloroaniline, are intermediates for agrochemical active ingredients, and the increasing demand for the latter causes an increasing demand for these intermediates.

The present invention relates to a new process of the above type, but not having the abovementioned disadvantages.

More precisely, the invention relates to a process for the preparation of optionally halogenated anilines of the general formula:

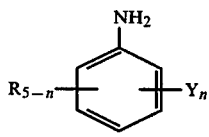

in which:

Y represents one or more identical or different halogen atoms,

R represents one or more substituents chosen from the group comprising a hydrogen atom, an alkyl radical containing from 1 to 4 carbon atoms or an alkoxy radical containing from 1 to 4 carbon atoms, and n is an integer from 0 to 5, by the ammonolysis of halogenobenzenes of the formula:

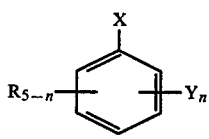

in which:

Y and R have the same meanings as above and

X represents a halogen atom, with an aqueous ammonia solution, in the presence of copper as a catalyst and of a complexing agent for the copper, which comprises using an 8-hydroxyquinoline derivative as the complexing agent.

The starting halogenobenzene compounds defined above include especially monohalogenobenzenes up to hexahalogenobenzenes, in particular trihalogenobenzenes and very particularly 1,3,5-trihalogenobenzenes. The halogen atoms in these compounds are especially bromine and iodine and preferably chlorine. Furthermore, the substitutent R is such that it does not substantially modify the ammonolysis process, and is preferably a hydrogen atom and/or a methyl and/or methoxy radical. Finally, n preferably has an integral value of 0 to 3.

The ammonolysis according to the invention is carried out by means of aqueous ammonia solution, which is preferably concentrated so that the reaction is carried out under economic conditions. This form of ammonia is not limiting, and any other aqueous composition which releases ammonia under equivalent conditions can be used. The amount of ammonia to be provided can be stoichiometric or less than stoichiometric, but is preferably more than stoichiometric, i.e. corresponds to a molar ratio to the starting material of 1/1 to 20/1 and preferably of 3/1 to 10/1.

The copper catalyst can be presented in the form of copper metal, of oxides or hydroxides or of cuprous or cupric salts of mineral or organic acids, in particular halides, and preferably chlorides, acetate, oxide or cyanide. Cuprous compounds are preferred. The catalyst is used in an amount of 0.08 to 30 mol % and preferably of 1 to 10 mol %, expressed as copper, relative to the starting material. This catalyst can be used on an inert support, but is preferably used as such in the medium. In fact, at the reaction temperature, it solubilises; this makes it possible to carry out the reaction under homogeneous catalysis.

The particular complexing agent according to the invention is an 8-hydroxyquinoline derivative. The term "8-hydroxyquinoline derivative" is understood as meaning 8-hydroxyquinoline itself and also its derivatives, in particular those substituted on the nucleus, such as e.g. 8-hydroxyquinoline-5-sulphonic acid. The addition of these compounds considerably improves the yield of the reaction, which is all the more surprising because very similar complexing agents, such as quinoline or 2-hydroxyquinoline, are scarcely more efficient than copper by itself. The particular complexing agent according to the invention is used in such a way that the molar ratio of complexing agent/copper is between 0.1/1 and 5/1 and preferably between 0.5/1 and 2/1.

Advantageously, the selectivity of the reaction can be improved by the addition, to the reaction medium, of a solvent for the halogenobenzene which is water-miscible and devoid of a deactivating effect on the copper. This solvent is generally used in an amount such that the weight ratio of solvent/starting halogenobenzene is between 0.1/1 and 10/1 and preferably between 0.5/1 and 4/1. The chemical nature of this solvent can vary. In particular, valuable results have been obtained preferably with N-methylpyrrolidone and tetramethylurea, but also with pyridine, ethanol, polyethylene glycols with molecular weights ranging from 400 to 1,500, and diglyme.

The process according to the invention is carried out at a relatively high temperature, generally at between 150° and 250° C. and preferably at between 170° and 220° C.

The total pressure, which is most frequently autogenous pressure, is generally between 10 and 70 bars and preferably between 20 and 50 bars.

The process according to the invention can be carried out continuously or batchwise. Because of the partial degrees of conversion, the reaction is preferably carried out continuously with recycling of the unconverted halogenobenzene or halogenobenzenes.

The final aniline is separated from the mixture in the usual manner, e.g. by hot filtration of the ammonium chloride formed, vapourisation of the ammonia and the water by letting down the pressure, it being possible for the ammonia and the water to be recycled, and then taking-up of the residual organic phase, either by a selective solvent for the halogenobenzene or by distillation. This gives the (halogeno)aniline in the desired purity.

The examples which follow are given by way of indication in order to illustrate the invention:

EXAMPLE 1

The following are introduced into a stirred autoclave: 1,3,5-trichlorobenzene (0.5 g), a 28% strength by weight aqueous ammonia solution (2.9 g), cuprous chloride (0.014 g, i.e. $1.5 \times 10^{-4}$ mol) and also (except for one experiment) a complexing agent ($1.5 \times 10^{-4}$ mol) of different types, i.e. respectively 8-hydroxyquinoline and 8-hydroxyquinoline-5-sulphonic acid as examples of complexing agents according to the invention, and thiourea and quinoline as examples of known complexing agents. The reaction mixture is heated to 200° C. and this temperature is maintained for 1 hour 20 minutes. The mixture is then allowed to cool, the pressure is brought back to atmospheric pressure, the mixture is diluted with water (10 ml) and extraction is carried out with isopropyl ether (2×13 ml). The resulting solution is subjected to analysis by vapour phase chromatography.

The table which follows collates the degree of conversion (DC%) of the 1,3,5-trichlorobenzene for each complexing agent used:

| Nature of the complexing agent | DC % |
| --- | --- |
| 8-Hydroxyquinoline | 39.4 |
| 8-Hydroxyquinoline-5-sulphonic acid | 53 |
| none (copper by itself) | 12.3 |
| Quinoline | 16.3 |
| Thiourea | 1.15 |

This table clearly shows that the increase in the degree of conversion with a complexing agent according to the invention is respectively more than 3-fold and 4-fold, compared with copper by itself or in the presence of a known complexing agent.

EXAMPLE 2

The procedure of Example 1 is repeated, except that the following mixture is used:

| 1,3,5-Trichlorobenzene | 1 g | ($5.5 \times 10^{-3}$ mol) |
| --- | --- | --- |
| 28% strength aqueous ammonia solution | 2.9 g | ($23 \times 10^{-3}$ mol) |
| Cuprous chloride | 0.03 g | ($0.3 \times 10^{-3}$ mol) |
| 8-Hydroxyquinoline | 0.042 g | ($0.3 \times 10^{-3}$ mol) |
| Solvent | 1 g | | the nature of the solvent being varied and experiments being carried out at 170°, 200° and 220° C. respectively.

The table which follows collates, for each solvent used, the degree of conversion of the 1,3,5-trichlorobenzene and also the molar yield of 3,5-dichloroaniline, relative to the 1,3,5-trichlorobenzene converted:

| Nature of the solvent | Temperature °C. | DC % | Y % |
| --- | --- | --- | --- |
| Tetramethylurea | 170 | 13.6 | 70.7 |
|  | 200 | 51.0 | 57.1 |
|  | 220 | 69.0 | 45.5 |
| Polyethylene glycol of molecular weight 400 | 170 | 17.7 | 61.5 |
|  | 200 | 47.3 | 48 |
|  | 220 | 68 | 38.7 |
| Pyridine | 200 | 40 | 62.2 |

EXAMPLE 3

Example 1 is repeated, except that the following mixture is used:

| 1,3,5-Trichlorobenzene | 1.0 g | ($5.5 \times 10^{-3}$ mol) |
| --- | --- | --- |
| 28% strength aqueous ammonia solution | 2.9 g | ($23 \times 10^{-3}$ mol) |
| Cuprous chloride | 0.03 g | ($0.3 \times 10^{-3}$ mol) |
| 8-Hydroxyquinoline | 0.084 g | ($0.6 \times 10^{-3}$ mol) |
| Ethanol | 2.0 g | | and that the reaction is carried out at 200° C.

Under these conditions, the degree of conversion of the 1,3,5-trichlorobenzene is 44% and the yield of 3,5-dichloroaniline is 70%, relative to the 1,3,5-trichlorobenzene converted.

EXAMPLE 4

Example 2 is repeated at 200° C. for 1 hour 20 minutes, the 8-hydroxyquinoline being replaced by the same number of mols of 8-hydroxyquinoline-5-sulphonic acid, and N-methylpyrrolidin-2-one being used.

Under these conditions, the degree of conversion of the 1,3,5-trichlorobenzene is 71.5% and the yield of 3,5-dichloroaniline is 60%, relative to the 1,3,5-trichlorobenzene converted.

EXAMPLE 5

Example 2 is repeated at 200° C. for 1 hour 20 minutes, except that the amounts of cuprous chloride and 8-hydroxyquinoline are doubled, the solvent being tetramethylurea.

Under these conditions, the degree of conversion is 76.4% and the yield of 3,5-dichloroaniline is 50%, relative to the 1,3,5-trichlorobenzene converted.

EXAMPLE 6

Example 1 is repeated, the following three mixtures being used:

| 1,3,5-Trichlorobenzene | 1.0 g |
| --- | --- |
| 28% strength aqueous ammonia solution | 2.9 g |
| Cuprous chloride | 0.03 g |
| 8-Hydroxyquinoline (in two cases) | 0.085 g |
| Tetramethylurea (in only one case) | 2.0 g |

The table which follows, collates, for each mixture, the degree of conversion of the 1,3,5-trichlorobenzene and the yield of 3,5-dichloroaniline, relative to the 1,3,5-trichlorobenzene converted.

| Mixture | 8-Hydroxyquinoline | Tetramethylurea | DC % | Y % |
|---|---|---|---|---|
| 6A | — | — | 16.1 | 47 |
| 6B | yes | — | 27.0 | 40 |
| 6C | yes | yes | 61.9 | 60 |

EXAMPLE 7

Example 1 is repeated, the following starting mixture being used:

| | | |
|---|---|---|
| Monochlorobenzene | 1.0 g | ($8.9 \times 10^{-3}$ mol) |
| 28% strength aqueous ammonia solution | 2.9 g | |
| Cuprous chloride | 0.03 g | ($3 \times 10^{-4}$ mol) |
| Complexing agent | | ($6 \times 10^{-4}$ mol) |
| Solvent | 2 g | |

The table which follows collates, for each experiment, the nature of the complexing agent and of the solvent and also the degree of conversion of the monochlorobenzene and the yield of aniline, relative to the monochlorobenzene converted:

| COMPLEXING AGENT | SOLVENT | DC % | Y % |
|---|---|---|---|
| — | — | 14.6 | 80.9 |
| 8-Hydroxyquinoline | ethanol | 23.5 | 72.2 |
| 8-Hydroxyquinoline-5-sulphonic acid | ethanol | 30.6 | 80.4 |
| 8-Hydroxyquinoline | tetramethylurea | 28.7 | 80.0 |
| 8-Hydroxyquinoline-5-sulphonic acid | tetramethylurea | 36.9 | 87.0 |
| 8-Hydroxyquinoline-5-sulphonic acid | tetramethylurea | 57.6 | 91.5 |

In this experiment, the reaction time was 2 hours 50 minutes.

This table clearly shows that the use of the complexing agent in association with the solvent makes it possible to improve the degree of conversion considerably, while at the same time maintaining a high level of yield Y.

I claim:

1. A process for the preparation of an optionally halogenated aniline of the general formula:

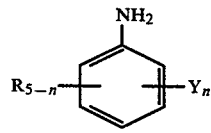

in which
Y represents one or more identical or different halogen atoms,
R represents one or more substituents chosen from the group comprising a hydrogen atom, an alkyl radical containing from 1 to 4 carbon atoms or an alkoxy radical containing from 1 to 4 carbon atoms, and
n is an integer from 0 to 5, by the ammonolysis of a halogenobenzene of the formula:

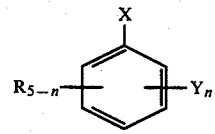

in which:
Y and R have the same meanings as above and
X represents a halogen atom, in the presence of copper as a catalyst and of a complexing agent for the copper, the improvement which comprises conducting the ammonolysis with an aqueous ammonia solution and using 8-hydroxyquinoline and/or an 8-hydroxyquinoline derivative as the complexing agent.

2. The process according to claim 1, wherein the complexing agent is 8-hydroxyquinoline.

3. The process according to claim 1, wherein the complexing agent is 8-hydroxyquinoline-5-sulphonic acid.

4. The process according to claim 1, 2, or 3, wherein the molar ratio of complexing agent/copper is between 0.1/1 and 5/1.

5. The process according to claim 4, wherein the molar ratio of complexing agent/copper is between 0.5/1 and 2/1.

6. The process according to claim 4, wherein the reaction medium also contains a solvent which is water-miscible and has no deactivating effect on the copper.

7. The process according to claim 6, wherein the solvent is chosen from the group comprising N-methylpyrrolidone, tetramethylurea, pyridine, a polyethylene glycol with a molecular weight of 400 to 1,500, ethanol and diglyme.

8. The process according to claim 6, wherein the weight ratio of solvent/halogenobenzene is between 0.1/1 and 10/1.

9. The process according to claim 8, wherein the weight ratio of solvent/halogenobenzene is between 0.5/1 and 4/1.

10. The process according to claim 1, 2 or 3, wherein X is a chlorine atom in the formulae.

11. The process according to claim 1, wherein Y is a chlorine atom in the formulae.

12. The process according to claim 1, wherein R is a hydrogen atom in the formulae.

13. The process according to claim 1, wherein n is an integer from 0 to 3.

14. The process according to claim 10, wherein X and Y are a chlorine atom and n is an integer from 0 to 3 in the formulae.

* * * * *